US011535891B2

(12) United States Patent
Green et al.

(10) Patent No.: US 11,535,891 B2
(45) Date of Patent: Dec. 27, 2022

(54) BARCODED SOLID SUPPORTS AND METHODS OF MAKING AND USING SAME

(71) Applicant: The Regents of the University of California, Oakland, CA (US)

(72) Inventors: Richard Green, Santa Cruz, CA (US); Balaji Sundararaman, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 16/865,061

(22) Filed: May 1, 2020

(65) Prior Publication Data

US 2020/0385800 A1  Dec. 10, 2020

Related U.S. Application Data

(60) Provisional application No. 62/843,076, filed on May 3, 2019.

(51) Int. Cl.
*C12Q 1/6874* (2018.01)
*G01N 33/487* (2006.01)

(52) U.S. Cl.
CPC ..... *C12Q 1/6874* (2013.01); *G01N 33/48721* (2013.01)

(58) Field of Classification Search
CPC ...... C12Q 1/6874; C12Q 1/6806; C12Q 1/68; G01N 33/48721
See application file for complete search history.

(56) References Cited

U.S. PATENT DOCUMENTS

| | | | |
|---|---|---|---|
| 2015/0376700 A1 | 12/2015 | Schnall-Levin et al. | |
| 2016/0046985 A1 | 2/2016 | Drmanac et al. | |
| 2018/0023119 A1 | 1/2018 | Adey et al. | |
| 2018/0044668 A1* | 2/2018 | Jiang | C40B 50/06 |

FOREIGN PATENT DOCUMENTS

WO   WO 2014145128   *  9/2014

OTHER PUBLICATIONS

Altschul et al. (1997) "Gapped BLAST and PSI-BLAST: a new generation of protein database search programs" Nucleic Acids Res. 25(17):3389-3402.
Green et al. (2010) "A Draft Sequence of the Neandertal Genome" Science 328(5979):710-722.
Karlin et al. (1993) "Applications and statistics for multiple high-scoring segments in molecular sequences" Proc. Natl. Acad. Sci. USA 90:5873-5877.
Miller et al. (2008) "Sequencing the nuclear genome of the extinct woolly mammoth" Nature 456(7220):387-390.
Macosko et al. (2015) "Highly Parallel Genome-wide Expression Profiling of Individual Cells Using Nanoliter Droplets" Cell 161, 1202-1214.
Poinar et al. (2006) "Metagenomics to Paleogenomics: Large-Scale Sequencing of Mammoth DNA" Science 311(5759):392-394.
Rasmussen et al. (2010) "Ancient human genome sequence of an extinct Palaeo-Eskimo" Nature 463(7282):757-762.
Stiller et al. (2006) "Patterns of nucleotide misincorporations during enzymatic amplification and direct large-scale sequencing of ancient DNA" Proc. Natl. Acad. Sci. 103(37):13578-13584.

* cited by examiner

*Primary Examiner* — Cynthia B Wilder
(74) *Attorney, Agent, or Firm* — Brian E. Davy; Bozicevic, Field & Francis LLP

(57) ABSTRACT

Aspects of the present disclosure include methods of making barcoded solid supports. In some embodiments, the methods include producing a concatemer by rolling circle amplification (RCA) of a circular nucleic acid template, where the circular nucleic acid template includes a barcode and a stem-loop forming region, and where the concatemer includes a plurality of linked units, each unit including the barcode and a stem-loop structure formed from the stem-loop forming region. Such methods further include disposing the concatemer on a solid support to produce a barcoded solid support including a plurality of the stem-loop structures extending from the surface of the solid support. The methods may further include treating the stem-loop structures with an agent that produces stem structures having ends compatible with target nucleic acids, and attaching the target nucleic acids to the stem structures. Barcoded solid supports and methods of using the barcoded solid supports are also provided.

16 Claims, 3 Drawing Sheets

Specification includes a Sequence Listing.

```
                        SEQUENCE LISTING

<160> NUMBER OF SEQ ID NOS: 8

<210> SEQ ID NO 1
<211> LENGTH: 14
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(7)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 1
nnnvnnnvnn nvnn                                                    14

<210> SEQ ID NO 2
<211> LENGTH: 130
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (48)..(50)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 2 ttttttttt acactctttc cctacacgac gctcttccga tctnnnvnnn vnnnvnngcg    60
cgcaagcttg cgcgctcact aaaggacgcg caagcttgcg cgccaggaaa cagctatgac   120
ttttttttt                                                          130
```

```
<210> SEQ ID NO 3
<211> LENGTH: 15
<212> TYPE: DNA
<213> ORGANISM: Artificial sequence
<220> FEATURE:
<223> OTHER INFORMATION: Synthetic polynucleotide

<400> SEQUENCE: 3
aaaaaaaaaa aaaaa                                                       15

<210> SEQ ID NO 4
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 4
gtcatagctg tttcctg                                                     17

<210> SEQ ID NO 5
<211> LENGTH: 26
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 5
agcttgccgv nnvnnnbnnb cgcgcg                                           26

<210> SEQ ID NO 6
<211> LENGTH: 26
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t

<400> SEQUENCE: 6
gatccgcgcg vnnvnnnbnn bcggca                                           26

<210> SEQ ID NO 7
<211> LENGTH: 34
<212> TYPE: DNA
<213> ORGANISM: Artificial sequence
<220> FEATURE:
<223> OTHER INFORMATION: Synthetic polynucleotide
```

```
<400> SEQUENCE: 7
gtgactggag ttcagacgtg tgctcttccg atct                                    34

<210> SEQ ID NO 8
<211> LENGTH: 16
<212> TYPE: DNA
<213> ORGANISM: Artificial sequence
<220> FEATURE:
<223> OTHER INFORMATION: Synthetic polynucleotide

<400> SEQUENCE: 8
gatcagatcg gaagag                                                        16
```

BARCODED SOLID SUPPORTS AND METHODS OF MAKING AND USING SAME

CROSS-REFERENCE TO RELATED APPLICATIONS

This application claims the benefit of U.S. Provisional Patent Application No. 62/843,076, filed May 3, 2019, which application is incorporated herein by reference in their entirety.
INCORPORATION BY REFERENCE OF SEQUENCE LISTING PROVIDED AS A TEXT FILE A Sequence Listing is provided herewith in a text file, UCSC-381 Seq List ST25, created on Aug. 5, 2020, and having a size of 3,157 bytes. The contents of the text file are incorporated herein by reference in its entirety.

INTRODUCTION

Diploid organisms have two copies of each autosome, which may have small or large genetic differences. Each version is called a haplotype, one copy inherited from the mother (maternal haplotype) and the other copy inherited from father (paternal haplotype). The two haplotypes combined form the genome. For current technologies, it is difficult to identify unique haplotypes within an individual genome. Resolving haplotypes is important for many applications including, but not limited to, diagnosis of genetic disorders (e.g., rare genetic disorders), diagnosis of cancer mutations, genotyping HLA for transplant matching, genome assembly (e.g., de novo genome assembly), etc.

Current technologies for resolving haplotypes (also known as "haplotype phasing") include tagging individual long DNA molecules with unique barcodes. The barcoded long molecules are then fragmented and sequenced using a short-read sequencing technique. In these "linked read" technologies, short reads that share a common barcode are "linked" to reconstruct the longer molecule. As a result, it is important to be able to introduce unique barcodes to an individual long DNA molecule (ideally up to the length of chromosome, but practically up to hundreds of kb to a few Mb long) throughout the length of the long DNA molecule.

The current state of the art involves two technologies for introducing unique barcodes onto long DNA molecules and fragmenting them for short-read sequencing. One such technology involves hydrogels loaded with primers containing barcodes that can randomly bind and amplify small fragments from a long DNA molecule. These primers contain barcodes that allow assembly of the smaller fragments to reconstruct sequence information of the original long DNA molecule after sequencing. This technique further involves physical separation of individual long DNA molecules by droplet formation and the addition of unique barcoded hydrogels to individual droplets. Physical separation is necessary to ensure an individual long DNA molecule is coupled with a unique barcode. See, e.g., U.S. Patent Application Publication No. US 2015/0376700. Another such technology involves the use of barcoded transposons loaded onto beads that can simultaneously fragment a long DNA molecule and incorporate barcodes into those fragments. See, e.g., U.S. Patent Application Publication Nos. US 2016/0046985 and US 2018/0023119. A major disadvantage of these methods is the requirement of long DNA molecules which are cumbersome to isolate. Phasing as well as structural variant detection depend on the input DNA size and ideally require up to hundreds of megabases. Isolation of long DNA molecules from fresh samples requires special skills and is impossible to recover from preserved samples like formalin-fixed-paraffin-embedded (FFPE) samples. For cancer diagnostic applications, FFPE samples are the major, if not sole, source of DNA from a patient's tumor.

SUMMARY

Aspects of the present disclosure include methods of making barcoded solid supports. In some embodiments, the methods include producing a concatemer by rolling circle amplification (RCA) of a circular nucleic acid template, where the circular nucleic acid template includes a barcode and a stem-loop forming region, and where the concatemer includes a plurality of linked units, each unit including the barcode and a stem-loop structure formed from the stem-loop forming region. Such methods further include disposing the concatemer on a solid support to produce a barcoded solid support including a plurality of the stem-loop structures extending from the surface of the solid support. The methods may further include treating the stem-loop structures with an agent that produces stem structures having ends compatible with target nucleic acids, and attaching the target nucleic acids to the stem structures. Barcoded solid supports and methods of using the barcoded solid supports are also provided.

DETAILED DESCRIPTION

Figure 1:
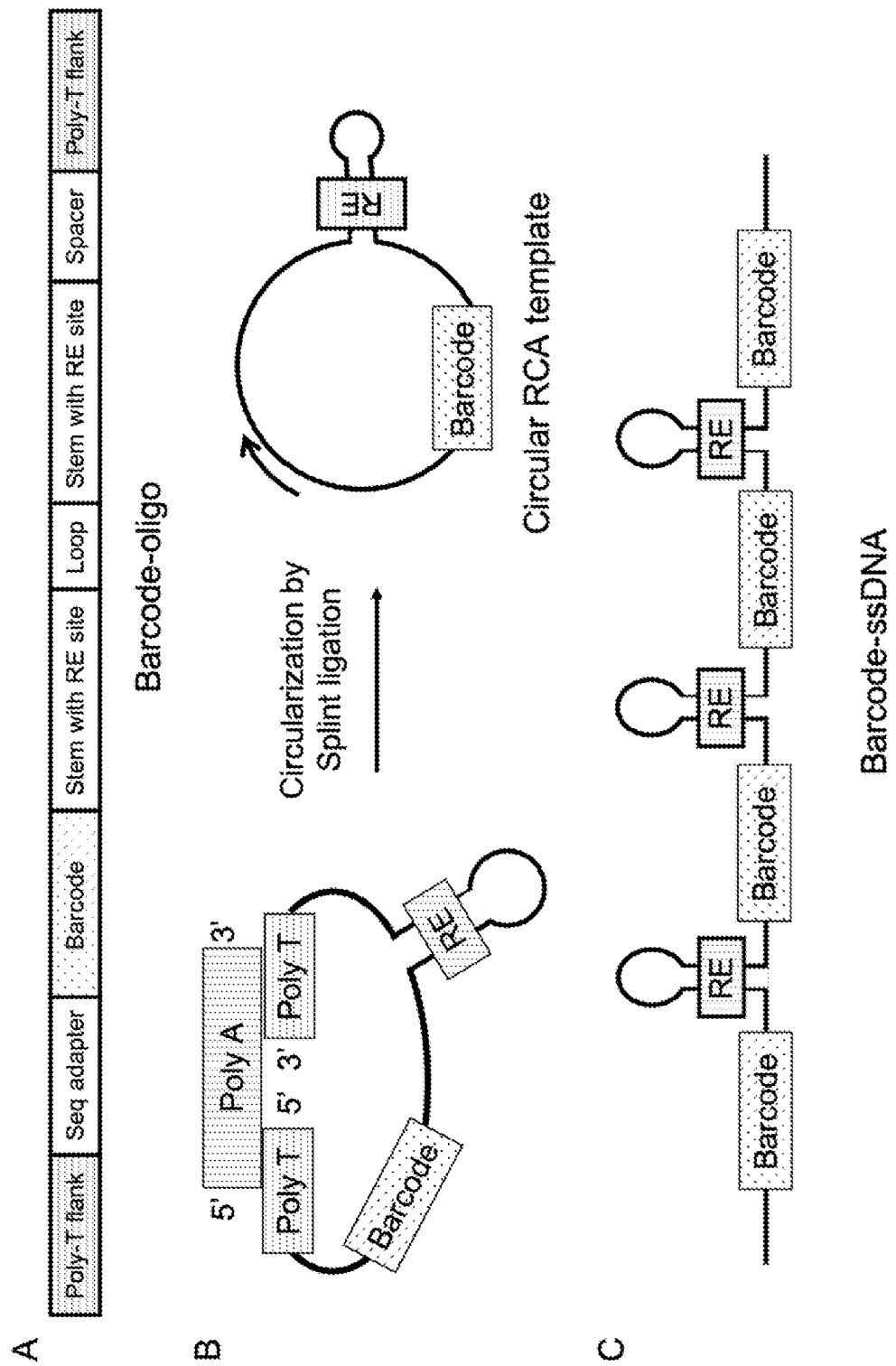
FIG. 1 Schematic illustration of a method of producing a concatemer that includes a plurality of linked units, each unit including a barcode and a stem-loop structure, according to one embodiment of the present disclosure.

Before the methods and solid supports of the present disclosure are described in greater detail, it is to be understood that the methods and solid supports are not limited to particular embodiments described, as such may, of course, vary. It is also to be understood that the terminology used herein is for the purpose of describing particular embodiments only, and is not intended to be limiting, since the scope of the methods and solid supports will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and solid supports. The upper and lower limits of these smaller ranges may independently be included in the smaller ranges and are also encompassed within the methods and solid supports, subject to any specifically excluded limit in the stated range. Where the stated range includes one or both of the limits, ranges excluding either or both of those included limits are also included in the methods and solid supports.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and solid supports belong. Although any methods and solid supports similar or equivalent to those described herein can also be used in the practice or testing of the methods and solid supports, representative illustrative methods and solid supports are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and solid supports are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and solid supports, which are, for clarity, described in the context of separate embodiments, may also be provided in combination in a single embodiment. Conversely, various features of the methods and solid supports, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and solid supports and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods of Making Barcoded Solid Supports

As summarized above, the present disclosure provides methods of making barcoded solid supports. According to some embodiments, the methods include producing a concatemer by rolling circle amplification (RCA) of a circular nucleic acid template, where the circular nucleic acid template includes a barcode and a stem-loop forming region, and where the concatemer includes a plurality of linked units, each unit including the barcode and a stem-loop structure formed from the stem-loop forming region. In certain embodiments, such methods further include disposing the concatemer on a solid support to produce a barcoded solid support including a plurality of the stem-loop structures extending from the surface of the solid support. Details regarding aspects of the methods are provided below.

The methods include producing a concatemer by rolling circle amplification of a circular nucleic acid template. As used herein, the term "rolling circle amplification" or "RCA" refers to an amplification (e.g., isothermal amplification) that generates linear concatemerized copies of a circular nucleic acid template using a strand-displacing polymerase. During RCA, the polymerase continuously adds single nucleotides to a primer (e.g., an oligonucleotide primer or a primer produced by nicking a double-stranded circular DNA (e.g., using an endonuclease)) annealed to the circular template which results in a concatemeric single-stranded DNA (ssDNA) that contains tandem repeats (or "linked units") (e.g., tens, hundreds, thousands, or more tandem repeats) complementary to the circular template. Suitable strand-displacing polymerases that may be employed include, but are not limited to, Phi29 polymerase, Bst polymerase, Vent exo-DNA polymerase, and the like. Reagents, protocols and kits for performing RCA are known and include, e.g., the RCA DNA Amplification Kit available from Molecular Cloning Laboratories; and TruePrime RCA Kit available from Expedeon. An example protocol for performing RCA to produce a concatemer according to some embodiments is provided in the Experimental section below.

The circular nucleic acid template, and in turn, each unit of the concatemer, includes a barcode. As used herein, a "barcode" or "barcode sequence" refers to an identifiable nucleotide sequence that can be coupled to a target nucleic acid (directly or indirectly). In some embodiments, a barcode is uniquely identifiable and may be used to identify the solid support to which the target nucleic acid is/was attached. Barcode sequences may vary widely in length and composition. According to some embodiments, the barcode has a degenerate sequence of from 4 to 120 nucleotides in length, e.g., from 4 to 100, 4 to 80, 4 to 60, 4 to 40, 6 to 30, 8 to 20 nucleotides, or 10 to 15 nucleotides in length. In certain embodiments, the barcode has a degenerate sequence of up to 20 nucleotides in length, e.g., 1, 2, 3, 4, 5, 6, 7, 8, 9, 10, 11, 12, 13, 14, 15, 16, 17, 18, 19 or 20 nucleotides in length. The barcode may include one or more mixed bases (e.g., every 3 bases, every 4 bases, or the like) of only three possible base combinations instead of four to prevent homopolymeric barcodes. For example, according to some embodiments, the barcode has the degenerate sequence NNNVNNNVNNNVNN (SEQ ID NO: 1), where N is A, T, C or G, and V can only be three of A, C or G.

The circular nucleic acid template further includes a stem-loop forming region such that each unit of the concatemer comprises a stem-loop structure. By "stem-loop structure" is meant a secondary nucleic acid structure that includes self-complementary inverted repeats and a non-self-complementary central region, where the self-complementary inverted repeats form a double-stranded stem and the non-self-complementary central region forms a single-stranded loop. In some embodiments, the stem-loop structure includes one or more enzyme-cleavable sites (e.g., one or more restriction enzyme sites), e.g., to facilitate the conversion of the stem-loop structure to a stem structure having an end (e.g., blunt end or overhang) compatible with a target nucleic acid (e.g., UMI, nucleic acid of interest, etc.) to be attached to the end of the stem structure.

In addition to the barcode and stem-loop structure, each unit of the concatemer may include one or more additional useful domains/regions and/or structures. For example, in certain embodiments, each unit includes a partial or complete sequencing adapter. By "sequencing adapter" is meant one or more nucleic acid domains that include at least a portion of a nucleic acid sequence (or complement thereof) utilized by a sequencing platform of interest, including but not limited to a sequencing platform provided by Illumina® (e.g., the iSeq™ sequencing system, MiSeq™ sequencing system, MiSeq™ sequencing system or NextSeq™ sequencing system); Oxford Nanopore™ Technologies (e.g., the MinION sequencing system, SmidgION sequencing system, GridION sequencing system or PromethION sequencing system), Ion Torrent™ (e.g., the Ion PGM™ sequencing system and/or Ion Proton™ sequencing system); Pacific Biosciences (e.g., the Sequel sequencing system or Sequel II sequencing system); Life Technologies™ (e.g., a SOLiD sequencing system); Roche (e.g., the 454 GS FLX+ sequencing system and/or GS Junior sequencing system); GenapSys sequencing system; BGISEQ-500 sequencing system or any other sequencing platform of interest.

In certain aspects, the sequencing adapter is, or includes, a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); an additional barcode domain (e.g., a domain that uniquely identifies the sample source of the nucleic acid being sequenced to enable sample multiplexing by marking every molecule from a given sample with a specific barcode or "tag"; such "barcode domain" typically is not the same as the barcodes described herein for use as barcoding solid supports); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof.

Other additional useful domains/regions and/or structures that may be included in the concatemer include a spacer region. A spacer region may be designed to provide a desired spacing/distance between adjacent stem-loop structures, where the number of nucleotides in the spacer region determines such spacing/distance. In certain embodiments, a spacer region is designed to include a priming site in the circular nucleic acid template for RCA (e.g., by isothermal amplification) to facilitate production of the concatemer. For example, such a spacer region may include a nucleotide sequence of sufficient complementarity to a primer used for RCA that the sequence serves as a priming site for the RCA.

The terms "complementary" or "complementarity" as used herein refer to a nucleotide sequence of a first nucleic acid that base-pairs by non-covalent bonds to a region of a second nucleic acid, or a nucleotide sequence of a first region of a nucleic acid that base-pairs by non-covalent bonds to a second region of the nucleic acid (e.g., a stem region). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" or "complementarity" refers to a nucleotide sequence that is at least partially complementary. These terms may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a region of a first nucleic acid may be perfectly (i.e., 100%) complementary to a region of a second nucleic acid, or the region of the first nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., *Proc. Natl. Acad. Sci.* USA 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

According to some embodiments, the methods further include, prior to producing the concatemer, producing the circular nucleic acid template by circularizing a linear nucleic acid comprising the barcode and the stem-loop forming region. Circularizing a linear nucleic acid may be performed using any suitable approach. In one example, the two ends of the linear nucleic acid are ligated to each other using a suitable ligase, e.g., a ligase suitable for blunt end ligation or sticky end ligation. Blunt end ligation could be employed by providing a blunt end at one end of the linear nucleic acid and a blunt end at the other end of the linear nucleic acid. Sticky end ligation could be employed by providing a sticky end at one end of the linear nucleic acid and a complementary sticky end at the other end of the linear nucleic acid.

In some embodiments, circularizing the linear nucleic acid is achieved by splint ligation. For example, the circularized DNA may be produced from a linear nucleic acid that includes a first sequence at a first end and a second sequence at the end opposite the first end, where circularization is achieved using a splint oligonucleotide that includes sequences complementary to the first and second sequences. According to some embodiments, a Gibson assembly approach or modified version thereof (e.g., NEBuilder Hifi DNA assembly) is used to join the ends of the linear nucleic acid using the splint oligonucleotide.

Subsequent to the circularization reaction and prior to RCA of the circular template, the circularization reaction mixture may be treated with a nuclease that only degrades linear DNA to remove any remaining (uncircularized) linear nucleic acid prior to RCA.

As used herein, an "oligonucleotide" is a single-stranded multimer of nucleotides from 5 to 500 nucleotides, e.g., 5 to 100 nucleotides. Oligonucleotides may be synthetic or may be made enzymatically, and, in some embodiments, are 5 to 50 nucleotides in length. Oligonucleotides may contain ribonucleotide monomers (i.e., may be oligoribonucleotides or "RNA oligonucleotides"), deoxyribonucleotide monomers (i.e., may be oligodeoxyribonucleotides or "DNA oligonucleotides"), or a combination thereof. Oligonucleotides may be 10 to 20, 20 to 30, 30 to 40, 40 to 50, 50 to 60, 60 to 70, 70 to 80, 80 to 100, 100 to 150 or 150 to 200, or up to 500 nucleotides in length, for example.

A method of producing a concatemer that includes a plurality of linked units, each unit including a barcode and a stem-loop structure, according to one embodiment is schematically illustrated in FIG. 1. Shown in panel A of FIG. 1 is a linear nucleic acid (designated in FIG. 1 and sometimes referred to herein as a "Barcode oligo") that includes the barcode and the stem-loop forming region, where the stem-loop forming region is collectively made up of a first stem region ("Stem with RE site"), a loop region ("Loop") and a second stem region ("Stem with RE site"). The stem regions include a recognition site for a restriction enzyme ("RE site"), which find use in producing stem structures having ends compatible for attachment to target nucleic acids (e.g., unique molecular identifiers, target nucleic acids of interest, etc.) as will be described in further detail below. Also in this example, the linear nucleic acid includes a spacer region for providing a desired spacing/distance between adjacent stem-loop structures in the subsequently produced concatemer, which spacer region may further include, e.g., a priming site for RCA (e.g., a primer binding site for isothermal amplification). Also in this example, the linear nucleic acid includes a sequencing adapter, which may be a partial or complete sequencing adapter (e.g., a partial Illumina P5 adapter).

Panel B (left) of FIG. 1 schematically illustrates an example approach for circularizing the linear nucleic acid shown in panel A. In this example, the linear nucleic acid has poly-T flanking regions ("Poly T") at each end, and circularization is achieved by splint ligation facilitated using a splint oligonucleotide ("Poly A") that hybridizes to the poly-T flanking regions and positions the ends of the poly-T flanking regions in proximity of each other for ligation using a suitable enzyme, e.g., a DNA ligase (e.g., T4 DNA ligase). Circularization produces the circular nucleic acid template for RCA as shown in panel B (right).

Panel C of FIG. 1 schematically illustrates the concatemer (designated as "Barcode-ssDNA" in FIG. 1) produced by RCA of the circular nucleic acid template shown in panel B (right). The concatemer includes a plurality of linked units, each unit including the barcode and a stem-loop structure formed from the stem-loop forming region. Although not labeled, in this example, each unit of the concatemer further includes the sequencing adapter, the spacer region, and a region made up of the flanking regions.

As summarized above, the methods of the present disclosure may further include disposing the concatemer on a solid support to produce a barcoded solid support including a plurality of the stem-loop structures extending from the surface of the solid support. DNA molecules tend to wrap around solid supports (e.g., beads) by unwrapping from globular structure in solution. According to some embodiments, the concatemer includes a plurality of first binding members, the solid support is functionalized with a plurality of second binding members having affinity for the first binding members, and disposing the concatemer on the solid support further includes binding the first binding members to the second binding members. In some embodiments, disposing the concatemer on the solid support includes non-covalently binding the first binding members to the second binding members. According to some embodiments, when the disposing includes non-covalently binding the first binding members to the second binding members, the first binding members include biotin and the second binding members include streptavidin, avidin, or anti-biotin antibodies. In certain embodiments, the first binding members are incorporated into the concatemer during RCA of the circular nucleic acid template. In one example, nucleotides that include the first binding members are incorporated into the concatemer during RCA of the circular nucleic acid template. Non-limiting examples of such nucleotides include biotinylated nucleotides.

In certain embodiments, when disposing the concatemer on the solid support includes binding first binding members of the concatemer to second binding members on the solid support, the first binding members are enriched in regions between the stem-loop structures of the concatemer. According to some embodiments, the first binding members being enriched in regions between the stem-loop structures facilitates extension of the stem-loop structures from the surface of the solid support. A variety of suitable approaches for enriching the first binding members in regions between the stem-loop structures may be employed. In certain embodiments, a linear nucleic acid which is circularized to produce the circular nucleic acid template for RCA is designed such that nucleotides having a particular base are enriched in regions between the stem-loop forming regions. RCA may subsequently be performed using nucleotides that base pair with the enriched nucleotides, where the nucleotides that base pair with the enriched nucleotides include one or more of the first binding members. By way of example, the circular nucleic acid template shown in FIG. 1 (panel B—right) includes a poly T region resulting from splint ligation of the poly-T flanking regions of the linear nucleic acid shown in panel A. When RCA is performed using dATPs that include one or more of the first binding members (e.g., biotinylated dATPs), the first binding members will be enriched in regions between the stem-loop structures in the resulting concatemer.

Figure 2:
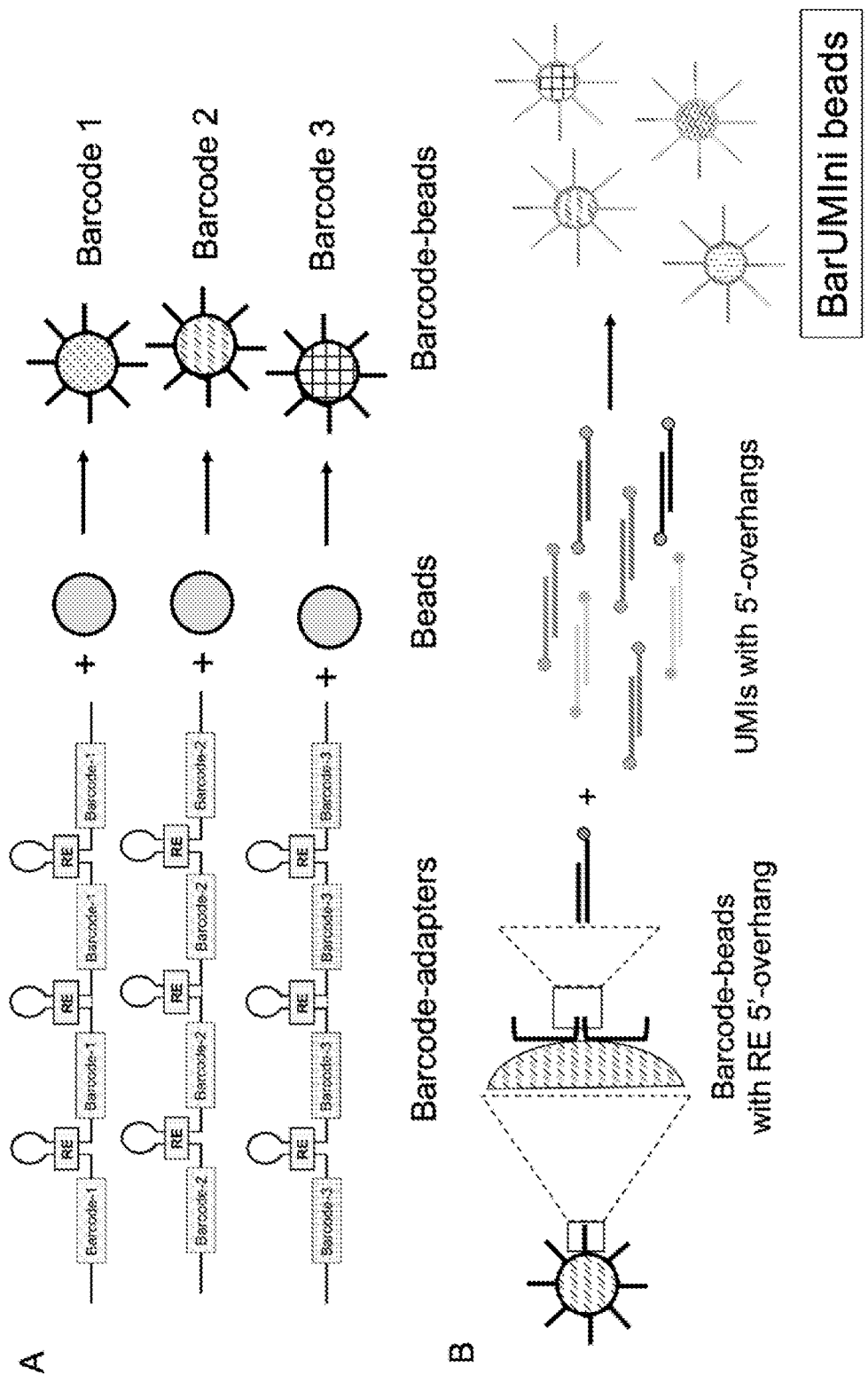
FIG. 2 Schematic illustration of disposing concatemers on solid supports in accordance with embodiments of the present disclosure (panel A) and production of barcoded solid supports (in this example, beads) that are individually identifiable by UMIs (panel B). Although the overhangs are 5' overhangs in the example shown in FIG. 2, the concatemer and UMIs may be designed to have compatible 5' overhangs or compatible 3' overhangs.

Disposing concatemers on solid supports in accordance with embodiments of the present disclosure is schematically illustrated in FIG. 2, panel A. In this example, three concatemers of a library of concatemers having degenerate barcodes (Barcode-1, Barcode-2 and Barcode-3 for the three concatemers shown) and stem-loop structures are disposed on solid supports (beads in this example) to produce barcoded solid supports that include a plurality of the stem-loop structures extending from the surface thereof.

As used herein, a "solid support" is an insoluble material upon which a concatemer may be disposed. In some embodiments, the solid support is a planar solid support. In other embodiments, the solid support is a particulate solid support, e.g., a bead. A particulate solid support may have any suitable shape, including but not limited to spherical, spheroid, rod-shaped, disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape. In certain aspects, a particulate solid support is a spherical or spheroid particle, e.g., a bead.

As used herein, the term "bead" refers to a small particulate solid support which may be generally spherical or spheroid in shape. In some embodiments, a bead or other type of particulate solid support has a longest dimension of from about 0.25 to about 200 microns, from about 0.5 to about 100 microns, from about 0.5 to about 25 microns, from about 0.5 to about 1.5 microns, or about 0.5 to about 1.0 micron in size, where "size" refers to the length of the longest dimension of the bead. A bead or other type of solid support may be magnetic or paramagnetic.

A variety of materials can be used as the solid support, e.g., bead. The support materials include any material that can act as a support for attachment of the molecules of interest. These materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutylene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, paramagnetic materials, etc.

According to some embodiments, the methods further include treating the stem-loop structures with an agent that produces stem structures having ends compatible with target nucleic acids. By "stem structure" is meant the product of treatment of a stem-loop structure where the treatment removes all or a portion of the loop of the stem-loop structure to produce ends compatible with the target nucleic acids. In certain embodiments, the target nucleic acids have blunt ends (at least at one end), and treating the stem-loop structures with the agent produces stem structures having blunt ends compatible with the target nucleic acids. According to some embodiments, the target nucleic acids have overhangs (at least at one end), and treating the stem-loop structures with the agent produces stem structures having overhangs compatible with the overhangs of the target nucleic acids.

In some embodiments, the stem-loop structures include a recognition site for a site-specific nucleic acid cleaving enzyme, and the treating includes contacting the stem-loop structures with the site-specific nucleic acid cleaving enzyme to produce stem structures having ends compatible with the target nucleic acids. Site-specific nucleic acid cleaving enzymes for which recognition sites may be provided in the stem-loop structures include, but are not limited to, site-specific endonucleases such as restriction endonucleases (e.g., type II restriction endonucleases) and homing endonucleases; guided nucleases such as CRISPR-associated (Cas) nucleases, Argonaute, Dicer, transcription activator-like effector nucleases (Talens), DNA glycosylases, DNA lyases, structure specific nucleases, or orthologs thereof. Site-specific nucleic acid cleaving enzymes used herein may be thermostable.

In certain embodiments, the target nucleic acids include a unique molecular identifier (UMI), genomic DNA, mitochondrial DNA (mtDNA), cell-free DNA (cfDNA), complementary DNA (cDNA), RNA, or any combination thereof.

The term "unique molecular identifier (UMI)" or "UMI" as used herein refers to a sequence of nucleotides which can be used to identify and/or distinguish one or more first molecules to which the UMI is attached from one or more second molecules. As used herein, a UMI may include one or more nucleotides at one or both ends of the identifying/distinguishing sequence of nucleotides, e.g., to facilitate attachment (e.g., ligation) of the UMI to a different nucleic acid (e.g., stem structure, nucleic acid of interest, and/or the like). UMIs are typically short, e.g., about 5 to 20 bases in length, and may be conjugated to one or more target molecules of interest or amplification products thereof. Generally, a UMI is used to distinguish between molecules of a similar type within a population or group, whereas a barcode sequence is used to distinguish between populations or groups of molecules. In some embodiments, where both a UMI and a nucleic acid barcode sequence are utilized, the UMI is shorter in sequence length than the nucleic acid barcode sequence. Attaching a UMI to the stem structures of a solid support finds use, e.g., in further increasing the diversity of the barcoded solid supports, tracking the number of copies of concatemers per solid support, and/or the like.

According to some embodiments, UMIs are formed by annealing forward and reverse oligonucleotides such that the formed UMIs have an overhang (e.g., a 5' or 3' overhang) compatible with the overhang of the stem structures. The UMI oligonucleotides may have a degenerate barcode flanked by sequences (e.g., direct GC repeats) that facilitate the annealing of the forward and reverse oligonucleotides. The sequences and annealing regions of the forward and reverse oligonucleotides may be designed such that the formed UMIs have two distinct/incompatible overhangs, thereby preventing concatenation of the oligonucleotides.

Shown in FIG. 2 (panel B) is the production of barcoded solid supports (in this example, beads) that are individually identifiable by UMIs (sometimes referred to herein as "BarUMIni beads"). In the example shown in FIG. 2, the UMIs are formed by annealing forward and reverse oligonucleotides such that the resulting UMIs have an overhang compatible with the overhang of the stem structures on the solid support. Although the overhangs are 5' overhangs in the example shown in FIG. 2, the concatemer and UMIs may be designed to have compatible 5' overhangs or compatible 3' overhangs. The barcoded solid supports (in this example, beads) that are individually identifiable by UMIs are produced by ligating (e.g., by enzymatic ligation) the compatible ends of the UMIs and stem structures. The UMIs may be designed such that the reverse oligonucleotide includes an overhang compatible with target nucleic acids of interest, e.g., genomic DNA having ends compatible with the overhang of the reverse oligonucleotide (e.g., for haplotype phasing, etc.), a poly-T stretch for capturing eukaryotic mRNA transcripts having poly-A tails, a Shine-Dalgarno sequence (AGGAGG) for capturing bacterial and archaeal RNAs, etc. Non-limiting examples of downstream applications facilitated by the barcoded solid supports are described in further detail below.

Accordingly, in certain embodiments, the methods further include attaching target nucleic acids to the stem structures. According to some embodiments, the attaching includes covalently linking the end of the stem structure to a compatible end of the target nucleic acid. A variety of suitable approaches are available for covalently linking nucleic acid molecules. In some embodiments, the linking is carried out using a chemical linking approach. In other embodiments, the linking is carried out using an enzymatic approach, such as enzymatically ligating the end of the stem structure to a compatible end of the target nucleic acid. Suitable reagents (e.g., ligases) and kits for performing such ligation reactions are known and available, e.g., the Instant Sticky-end Ligase Master Mix available from New England Biolabs (Ipswich, Mass.). Ligases that may be employed include, e.g., T4 DNA ligase (e.g., at low or high concentration), T4 DNA ligase, T7 DNA Ligase, *E. coli* DNA Ligase, Electro Ligase®, or the like. Conditions suitable for performing the ligation reaction will vary depending upon the type of ligase used. Information regarding such conditions is readily available.

In some embodiments, the methods include covalently attaching (e.g., ligating) UMIs to the stem structures, e.g., as illustrated in FIG. 2 (panel B). When the methods include covalently attaching UMIs to the stem structures, such methods may further include covalently attaching (e.g., ligating) nucleic acids (e.g., nucleic acids of interest to be analyzed in a downstream application) to the distal end of the UMIs. As used herein, the "distal" end of a nucleic acid (e.g., a UMI, nucleic acid of interest, etc.) is the end of the nucleic acid opposite the stem structure, while the "proximal" end of a nucleic acid is the end closest to the stem structure, e.g., the end that is attached directly or indirectly to the stem structure. In certain embodiments, the nucleic acids ligated to the distal end of the UMIs comprise genomic DNA, mitochondrial DNA (mtDNA), cell-free DNA (cfDNA), complementary DNA (cDNA), RNA, or any combination thereof.

In some embodiments, the methods include covalently attaching (e.g., ligating) nucleic acids other than UMIs to the stem structures. For example, the methods may include covalently attaching genomic DNA, mitochondrial DNA (mtDNA), cell-free DNA (cfDNA), complementary DNA (cDNA), RNA, or any combination thereof, to the stem structures. According to such embodiments, the nucleic acids other than UMIs have a UMI attached to the distal end of the nucleic acids prior to attaching the proximal end of the nucleic acids to the stem structures. In other embodiments, the methods include covalently attaching (e.g., ligating) nucleic acids other than UMIs to the stem structures, and subsequently attaching a UMI to the distal ends of the nucleic acids attached to the stem structures. In still other embodiments, the methods do not include attaching a UMI to the stem structures or nucleic acids at all, where such a UMI is not necessary in the downstream application of interest.

Nucleic acids to be attached to the stem structures (directly or via a UMI) may be any nucleic acids of interest. The nucleic acids may be polymers of any length composed of deoxyribonucleotides, ribonucleotides, or combinations thereof, e.g., 10 bases or longer, 20 bases or longer, 50 bases or longer, 100 bases or longer, 500 bases or longer, 1,000 bases or longer, 2,000 bases or longer, 3,000 bases or longer, 4,000 bases or longer, 5,000 bases or longer, 10,000 bases or longer, 100,000 bases or longer, 1 million bases or longer, or more bases. In certain aspects, the nucleic acids are polymers composed of deoxyribonucleotides or ribonucleotides, e.g., 10 bases or less, 20 bases or less, 50 bases or less, 100 bases or less, 500 bases or less, 1000 bases or less, 2000 bases or less, 3000 bases or less, 4000 bases or less, or 5000 bases or less.

In certain aspects, the nucleic acids attached to the stem structures (directly or via a UMI) are deoxyribonucleic acids (DNAs). DNAs of interest include, but are not limited to, genomic DNA (including genomic DNA fragments), mitochondrial DNA (mtDNA), complementary DNA (or "cDNA") synthesized from any RNA or DNA of interest, recombinant DNA (e.g., plasmid DNA), or the like.

According to certain embodiments, the nucleic acids attached to the stem structures (directly or via a UMI) are ribonucleic acids (RNAs). RNAs of interest include, but are not limited to, messenger RNA (mRNA), microRNA (miRNA), small interfering RNA (siRNA), CRISPR guide RNA, transacting small interfering RNA (ta-siRNA), natural small interfering RNA (nat-siRNA), ribosomal RNA (rRNA), transfer RNA (tRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, ribozyme, or any combination of such RNA types or subtypes.

In some embodiments, the nucleic acids attached to the stem structures are from a degraded nucleic acid sample. As used herein, a "degraded nucleic acid sample" is a sample of DNA that has been fragmented by enzymatic, physical, chemical or other processes. Examples of degraded nucleic acid samples are the DNA fragments recovered from bone remains, hair, cell-free DNA from blood plasma, or environmental DNA recovered from soil or water. In certain aspects, when the nucleic acids are from a degraded nucleic acid sample, the nucleic acids are from an ancient nucleic acid sample. By "ancient nucleic acid sample" is meant nucleic acid fragments recovered from biological remains. A non-limiting example of an ancient nucleic acid sample of interest is a nucleic acid sample obtained (e.g., isolated) from an extinct organism or animal, e.g., an extinct mammal. In certain embodiments, the extinct mammal is from the genus *Homo*. In some embodiments, the nucleic acids are from a forensic nucleic acid sample. As used herein, a "forensic nucleic acid sample" is a nucleic acid sample relating to (e.g., obtained during the course of) the investigation of a crime, e.g., semen, blood, and/or the like.

According to certain embodiments, the nucleic acids attached to the stem structures are cell-free nucleic acids, e.g., cell-free DNA (cfDNA), cell-free RNA (cfRNA), or both. Such cell-free nucleic acids may be obtained from any suitable source. In certain aspects, the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, and stool. In some embodiments, the cell-free nucleic acids are cell-free fetal DNAs. In certain aspects, the cell-free nucleic acids are circulating tumor DNAs.

The nucleic acids attached to the stem structures may be tumor nucleic acids (that is, nucleic acids isolated from a tumor). "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like. According to some embodiments, the nucleic acids to be attached to the stem structures are nucleic acids from circulating tumor cells (CTCs). By "circulating tumor cell" or "CTC" is meant a cell that has shed into the vasculature from a primary tumor and circulates in the bloodstream. The circulating tumor cell may be present in a cellular sample (e.g., a biological fluid sample, such as a blood sample or fraction thereof) obtained from a mammal (e.g., a human cancer patient), e.g., with an epithelial cell cancer, such as breast, prostate, lung, colon, or pancreatic cancer.

In some embodiments, DNA or RNA attached to the stem structures (directly or via a UMI) is from fixed cells, e.g., fixed tissue, such as formalin-fixed tissue. In some embodiments, such DNA or RNA is isolated from formalin-fixed paraffin embedded (FFPE) cells, e.g., FFPE tissue.

In some embodiments, the nucleic acids attached to the stem structures are fixed using a suitable fixative (e.g., with formaldehyde, such as 1% formaldehyde) to preserve the architecture of the of the nucleic acid when it is attached to the solid support. For example, when the nucleic acid is genomic DNA and the source of the genomic DNA is a live cell or tissue, the genomic DNA may be fixed (e.g., prior to or subsequent to extraction from the cell or tissue) to preserve the architecture of the genomic DNA. Such embodiments find use, e.g., to increase the likelihood that genomic DNAs attached to stem structures of a particular solid support (having a particular barcode) originated from the same cell and/or chromosome, such that different genomic sequences associated with the same barcode may be traced back to the same solid support, and in turn, the same cell and/or chromosome.

Nucleic acids to be attached to the stem structures may be prepared from any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of an animal. In some embodiments, the animal is a mammal, e.g., a mammal from the genus *Homo*, a non-human primate, a human, a rodent (e.g., a mouse or rat), a dog, a cat, a horse, a cow, or any other mammal of interest. In other embodiments, the nucleic acid sample is isolated/obtained from a source other than a mammal, such as bacteria, archae, yeast, insects (e.g., *drosophila*), amphibians (e.g., frogs (e.g., *Xenopus*)), viruses, plants, or any other non-mammalian nucleic acid sample source.

The nucleic acid sample may be obtained (e.g., isolated) from an extant organism or animal. In other aspects, however, the nucleic acid sample may be obtained (e.g., isolated) from an extinct (or "ancient") organism or animal, e.g., an extinct mammal, such as an extinct mammal from the genus *Homo*.

Approaches, reagents and kits for isolating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md.); the DNAzol®, ChargeSwitch®, Purelink®, GeneCatcher® nucleic acid isolation/purification kits by Life Technologies, Inc. (Carlsbad, Calif.); the NucleoMag®, NucleoSpin®, and NucleoBond® nucleic acid isolation/purification kits by Clontech Laboratories, Inc. (Mountain View, Calif.). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

When an organism, plant, animal, etc. from which the nucleic acid sample is obtained (e.g., isolated) is extinct (or "ancient"), suitable strategies for recovering such nucleic acids are known and include, e.g., those described in Green et al. (2010) *Science* 328(5979):710-722; Poinar et al. (2006) *Science* 311(5759):392-394; Stiller et al. (2006) *Proc. Natl. Acad. Sci.* 103(37):13578-13584; Miller et al. (2008) *Nature* 456(7220):387-90; Rasmussen et al. (2010) *Nature* 463(7282):757-762; and elsewhere.

In some embodiments, the methods include producing a library of barcoded solid supports, e.g., beads. For example, the methods may further include using a library of circular nucleic acid templates that include degenerate barcodes to produce a library of barcoded solid supports including degenerate barcodes. A library of linear nucleic acids that include a stem-loop forming region and degenerate barcodes may be produced by degenerate nucleic acid synthesis. The barcodes may be of any length, including any of the lengths described elsewhere herein. A library of circular nucleic acid templates may be produced from such linear nucleic acids (e.g., by splint ligation as described above), a library of concatemers may be produced by RCA of such circular nucleic acid templates, and a library of barcoded solid supports may be produced by disposing concatemers of the concatemer library on solid supports, e.g., beads.

Barcoded Solid Supports

Also provided by the present disclosure are barcoded solid supports. In some embodiments, provided are barcoded solid supports produced according to any of the methods of the present disclosure for making barcoded solid supports, including any of the methods described in the preceding section entitled Methods of Making Barcoded Solid Supports. Such barcoded solid supports may have any of the features described in the preceding section (e.g., types of solid supports, barcodes, target nucleic acids (e.g., UMIs and/or nucleic acids of interest for downstream analysis, etc.), which features are incorporated but not reiterated herein for purposes of brevity. According to some embodiments, provided are libraries of barcoded solid supports. In some embodiments, provided is a library of barcoded solid supports produced using a library of circular nucleic acid templates that include degenerate barcodes to produce a library of barcoded solid supports including degenerate barcodes, as described above.

In certain embodiments, provided is a barcoded solid support that includes a concatemer disposed on a solid support (e.g., a bead), where the concatemer includes a plurality of linked units, each unit including a barcode and a stem-loop structure, and where a plurality of the stem-loop structures extend from the surface of the solid support.

Additional barcoded supports are also provided. For example, also provided are barcoded solid supports (e.g., beads) that include a concatemer disposed on a solid support, where the concatemer includes a plurality of linked units, each unit including a barcode, a stem structure, and a nucleic acid attached (e.g., ligated) to the stem structure, where a plurality of the stem structures and attached nucleic acids extend from the surface of the solid support. In some embodiments, the nucleic acid attached to the stem structure is a UMI. An example of such an embodiment is schematically illustrated in FIG. 2 (panel B—right, designated therein as "BarUMIni beads"). In some embodiments, when the nucleic acid attached to the stem structure is a UMI, a further nucleic acid is attached to the distal end of the UMI. The further nucleic acid may be, e.g., genomic DNA, mitochondrial DNA (mtDNA), cell-free DNA (cfDNA), complementary DNA (cDNA), or RNA, including any of the particular types of DNAs and RNAs described in the preceding Methods section.

In some embodiments, the nucleic acid attached (e.g., ligated) to the stem structure is a nucleic acid other than a UMI. For example, the nucleic acid attached to the stem structure may be a genomic DNA, mitochondrial DNA (mtDNA), cell-free DNA (cfDNA), complementary DNA (cDNA), or RNA, including any of the particular types of DNAs and RNAs described in the preceding Methods section. In some embodiments, when the nucleic acid attached to the stem structure is a nucleic acid other than a UMI, a further nucleic acid is attached to the distal end of the nucleic acid other than a UMI. For example, a UMI may be attached to the distal end of the nucleic acid other than a UMI.

According to any of the barcoded solid supports of the present disclosure, in some embodiments, the concatemer includes a plurality of first binding members, the solid support is functionalized with a plurality of second binding members having affinity for the first binding members, and the first binding members are bound to the second binding members. According to some embodiments, the first binding members are non-covalently bound to the second binding members. In certain embodiments, when the first binding members are non-covalently bound to the second binding members, the first binding members include biotin and the second binding members include streptavidin, avidin, or anti-biotin antibodies. In certain embodiments, the first binding members are present in the concatemer in the form of biotinylated nucleotides. When the concatemer includes a plurality of first binding members, the first binding members may be enriched in regions between the stem-loop structures. According to some embodiments, the first binding members being enriched in regions between the stem-loop structures facilitates extension of the stem-loop structures from the surface of the solid support. Non-limiting examples of approaches for enriching the first binding members in regions between the stem-loop structures are described in the preceding Methods section.

In addition to the barcode and stem-loop structure, each unit of the concatemer of any of the barcoded solid supports described above may include one or more additional useful domains/regions and/or structures. For example, in certain embodiments, each unit includes a partial or complete sequencing adapter, e.g., when it is desirable to sequence a nucleic acid of interested attached (directly or via a UMI) to a stem structure.

Also provided are libraries of any of the barcoded solid supports of the present disclosure, where the barcoded solid supports of the library include degenerate barcodes.

Methods of Analyzing Nucleic Acids

As summarized above, the present disclosure also provides methods of analyzing nucleic acids. In certain embodiments, the methods include providing a barcoded solid support (e.g., a barcoded bead), the barcoded solid support including a concatemer disposed on the solid support, the concatemer including a plurality of linked units, each unit including a barcode and a stem structure, where a plurality of the stem structures extend from the surface of the solid support. Such methods further include attaching nucleic acids of interest to the stem structures, and analyzing the nucleic acids of interest attached to the stem structures.

In some embodiments, the nucleic acids of interest are attached (e.g., ligated) directly to the distal end of the stem structures. In other embodiments, the nucleic acids of interest are attached indirectly (e.g., via a UMI) to the stem structures. Accordingly, in some embodiments, UMIs are attached to the distal ends of the stem structures, and attaching the nucleic acids of interest to the stem structures includes attaching the nucleic acids of interest to the distal ends of the UMIs—either before or subsequent to attachment of the UMIs to the distal ends of the stem structures.

In some embodiments the nucleic acids of interest are attached directly to the distal ends of the stem structures. According to such embodiments, a UMI may be attached to the distal end of the nucleic acid of interest—either before or subsequent to attachment of the nucleic acid of interest to the distal end of the stem structure.

As will be appreciated with the benefit of the present disclosure, the barcoded solid supports (e.g., barcoded beads) of the present disclosure may be employed to facilitate a wide variety of downstream applications, non-limiting examples of which will now be described.

Nucleic Acid Sequencing

Nucleic acids of interest attached to the stem structures of the barcoded solid supports may be analyzed by nucleic acid sequencing. In some embodiments, a nucleic acid including the nucleic acid of interest or portion thereof, the barcode of the concatemer, and any other optional useful domains (e.g., partial or complete sequencing adapter and/or UMI) is cleaved (e.g., using a restriction enzyme) from the solid support, and the cleaved nucleic acid or amplicons thereof may be sequenced using a suitable nucleic acid sequencing system to obtain sequence information for the nucleic acid of interest, where the obtained sequencing read further includes the barcode sequence such that the nucleic acid of interest may be traced back to the bead to which it was previously attached. The nucleic acid cleaved from the solid support may include a UMI (e.g., disposed between the nucleic acid of interest and the stem structure, or attached to the distal end of the nucleic acid of interest), such that the sequencing read will further include the UMI sequence.

According to certain embodiments, the nucleic acid of interest or portion thereof, the barcode of the concatemer, and any other optional useful domains (e.g., partial or complete sequencing adapter and/or UMI) are PCR amplified while disposed on the solid support, and the resulting amplicons are sequenced using a suitable nucleic acid sequencing system to obtain sequence information for the nucleic acid of interest, where the obtained sequencing read further includes the barcode sequence such that the nucleic acid of interest may be traced back to the bead to which it was previously attached. The amplicons may include a UMI (e.g., amplified from a UMI disposed between the nucleic acid of interest and the stem structure, or attached to the distal end of the nucleic acid of interest), such that the sequencing read will further include the UMI sequence.

Sequence information obtained by sequencing the nucleic acids of interest and associated barcoded (and optionally, an associated UMI) may be used in a wide variety of research and clinical contexts. The sequence information finds use in any application in which obtaining "linked reads" (that is—different reads having the same barcode sequence) is informative. In some embodiments, the sequence information is used to diagnose a subject as having a particular medical condition, genetic disorder, and/or the like. The sequence information can be used for de novo genome assembly, haplotype phasing, HLA typing, etc.

Sequencing may be carried out using any suitable sequencing system, examples of which include sequencing systems available from Illumina® (e.g., the iSeq™ sequencing system, MiSeq™ sequencing system, MiSeq™ sequencing system or NextSeq™ sequencing system); Oxford Nanopore™ Technologies (e.g., the MinION sequencing system, SmidgION sequencing system, GridION sequencing system or PromethION sequencing system), Ion Torrent™ (e.g., the Ion PGM™ sequencing system and/or Ion Proton™ sequencing system); Pacific Biosciences (e.g., the Sequel sequencing system or Sequel II sequencing system); Life Technologies™ (e.g., a SOLiD sequencing system); Roche (e.g., the 454 GS FLX+ sequencing system and/or GS Junior sequencing system). Detailed protocols for preparing nucleic acids for sequencing, and for obtaining sequencing reads using a particular sequencing platform, are readily available from the manufacturers of the sequencing systems.

Haplotype Phasing

The barcoded solid supports of the present disclosure may be employed for haplotype phasing. A detailed example protocol is provided in the Experimental section below. Briefly, in some embodiments, live cells or tissue is crosslinked to preserve the contiguity and proximity of haplotypes and other higher order chromosomal interactions. The genomic DNA is ligated to the stem structures of barcoded beads and then extracted from chromatin protein complexes by digestion with a protease (e.g., Proteinase K) in a crosslink removal step. The eluted library is then PCR amplified and the resulting amplicons are sequenced. The sequencing data may be aligned to a reference genome. Sequencing reads having the same barcode (that is "linked reads") are assigned to "barcode-islands" in the genome which indicate that these reads originated from same barcoded solid support and are part of the initial long DNA molecule. Overlapping barcode-islands may be merged to form contigs or phase blocks. Continuous overlapping contigs may be assembled to obtain haplotypes.

Other Applications

Other non-limiting applications for which the barcoded solid supports of the present disclosure may be employed will now be described.

Barcoded solid supports (e.g., beads) having a compatible restriction enzyme (RE) overhangs may be used for identification of structural variations in the genome, topologically associated domains (TADs) and chromatin architecture, haplotype phasing, and genome assembly. Input material for this application can be isolated or cultured cells, blood, tissue, FFPE samples, any other preserved samples, etc. Multiple read-pairs having the same barcode and mapping to the same chromosome are called linked-reads and form barcode-islands. Continuous overlapping barcode-islands are joined to form contigs which are then used to reconstruct haplotypes. Barcode-islands with a long gap in one contig matching with a continuous barcode-island in another homologous contig would indicate structural variations (long insertion/deletions) between two haplotypes. Chimeric reads formed by read-pairs mapping to two distinct chromosomes that have the same barcode would indicate either structural variation (fusion and translocation) or topologically associated domain (TADs) of two distinct chromosomes.

Barcoded solid supports (e.g., beads) having a compatible restriction enzyme (RE) overhangs may be used for single cell genome sequencing, e.g., to study cancer clonal populations and population genomics. Barcoded solid supports combined with single-cell partitioning techniques like microfluidic devices or emulsion PCR can be used for single cell genome sequencing. Reads having distinct barcodes indicate single cell origin and comparative genomics can be used for analyzing SNVs and mutational status of distinct tumor cell populations. Single cell genomic DNA analysis can also be applied for microbial population genetics and metagenomic analysis.

Barcoded solid supports having bait sequences in the overhangs can be used to capture and enrich target sequences which can be used, e.g., for HLA typing, exome capture, mitochondrial DNA enrichment and custom gene panels for cancer diagnostics. Input material for this application can be DNA isolated from purified organelles, cell-free DNA (cfDNA) isolated from purified exosomes, blood or liquid biopsy, single cells, blood, tissue, FFPE samples, or any other sources from patients, non-patient individuals, etc. Reads with distinct barcodes can be used to distinguish individual organelles, cells and samples. Capturing target sequences using bait sequences of either exomes or custom gene panels would facilitate ultra-deep sequencing, e.g., to analyze rare SNVs among distinct tumor cells. Mitochondrial DNA (mtDNA) capture combined with separation of individual organelles can be used to analyze mtDNA diversity within cells and samples derived from individual organisms. mtDNA sequencing would also facilitate analysis of the mutational burden of individual mitochondrion that are implicated in genetic and neurological disorders. Barcoded solid supports having HLA bait sequences combined with linked reads derived from crosslinked chromatin can be used for phasing and typing of individual HLA loci.

Barcoded solid supports having poly-T overhangs can be used to capture poly-A containing eukaryotic RNA for transcriptome analysis and single cell RNA-sequencing. Input material for this application can be RNA isolated from either bulk samples like blood, tissue, FFPE samples or single cell and subcellular sources like purified organelles, cell-free circulating RNA isolated from purified exosomes or any other sources from patients, non-patient individuals, etc. BarUMIni beads having a poly-T stretch bait sequence and 3' UTR of transcripts of interest can be used for targeted RNA-sequencing. Data from this application will have sequence information of transcripts at their 3' end and can be used for expression analysis of targeted transcripts.

Barcoded solid supports having the Shine-Dalgarno (SD) sequence (AGGAGG) can be used to capture bacterial and archaeal mRNA for application in metatranscriptomics and biome analysis. Input material for this application can be RNA isolated from environmental samples for metatranscriptome analysis. Sequence data from this application will contain the 5' end of transcripts that have the SD sequence. Transcriptome diversity and expression levels can be used to analyze microbial diversity and activity in an environmental sample.

Figure 3:
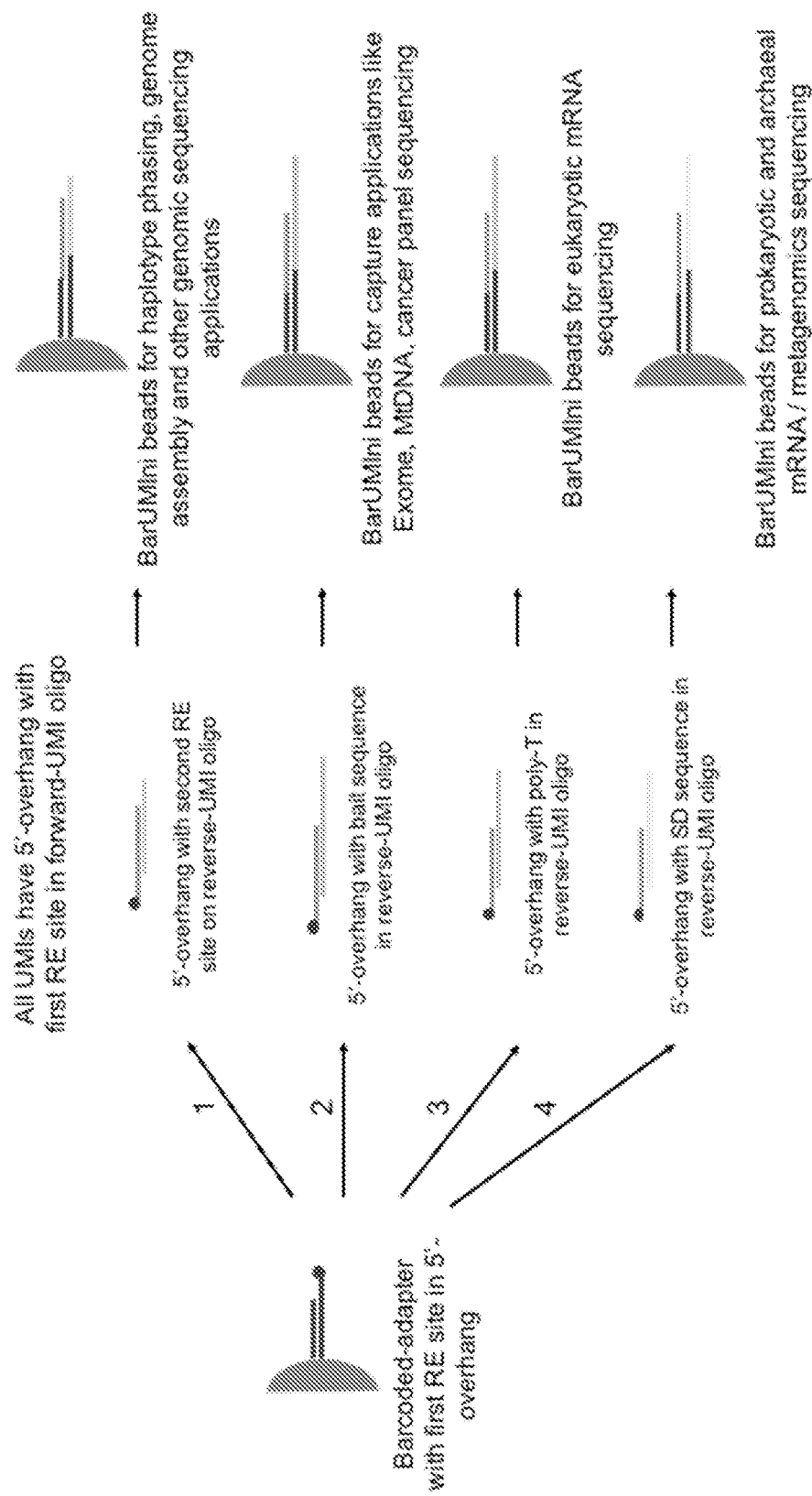
FIG. 3 Schematic illustrations of certain applications of the barcoded solid supports of the present disclosure. In these examples, unique molecular identifiers (UMIs) are attached to stem structures of the barcoded solid supports via compatible overhangs, and the UMIs have overhangs on their distal ends which vary depending upon the type of nucleic acid of interest to be analyzed. Although the overhangs are 5' overhangs in the example shown in FIG. 3, the concatemer, UMIs, and ends of the nucleic acids of interest may be designed to have compatible 5' overhangs or compatible 3' overhangs. (1) Reverse-UMI oligo with a second restriction enzyme (RE) site can be used for phasing, genome assembly, and other genomic DNA sequencing applications. (2) Reverse-UMI oligo with a bait sequence can be used for capture applications like exome sequencing, mitochondrial DNA sequencing, and custom gene panel sequencing, e.g., for cancer diagnostics. (3) Reverse-UMI oligo with a poly-T overhang can be used for mRNA sequencing. (4) Reverse-UMI oligo with a Shine-Dalgarno (SD) sequence can be used in microbiome analysis.

Non-limiting embodiments are schematically illustrated in FIG. 3. Although the overhangs are 5' overhangs in the examples shown in FIG. 3, the concatemer, UMIs, and ends of the nucleic acids of interest may be designed to have compatible 5' overhangs or compatible 3' overhangs.

The following examples are offered by way of illustration and not by way of limitation.

EXPERIMENTAL

Example 1—Generation of Barcoded Beads

The present example is a non-limiting example of an approach for generating barcoded solid supports (in this example, barcoded beads).

50 pmol of 5' phosphorylated Barumini_v2b linear oligo was annealed with 150 pmol splint oligo (dA15) to create a head-to-tail circle. A DNA nick in the circle was ligated using 4000 U T4 DNA ligase at 23° C. for 10 min. Unligated linear oligos were digested with exonucleases I and III and the circular oligo template was column purified.

The circular oligo template was amplified using an RCA reaction detailed below with phi29 DNA polymerase at 30° C. for 30 min. RCA performed either with Barumini_RCA_v2 oligo targeting the spacer region of the template or dA15 oligo as primer.

| | | |
|---|---|---|
| Circularized oligo template | 2.7 ul | ~1 pmol |
| 10× Phi29 buffer | 5.0 ul | 1× |

-continued

| | | |
|---|---|---|
| dGTP, dCTP, dTTP mix-25 mM each | 1.0 ul | 25 nmol (500 uM) each |
| dATP-20 mM | 1.2 ul | 23 nmol (460 uM) |
| bioting-11-dATP-1 mM (PerkinElmer) | 2.0 ul | 2 nmol (40 uM) |
| 10 uM primer (Barumini_RCA_v2 or dA15) | 1.0 ul | 10 pmol |
| Phi29 | 2.0 ul | 20 U |
| 10 mg/ml BSA | 1.0 ul | 200 ug/ml |
| H2O | 34.2 ul | |
| Total | 50.0 ul | |

RCA products were 1× SPRI bead cleaned, and analyzed in a Fragment Analyzer to assess the length and yield of concatemers of barcodes. The RCA reaction performed using a dA15 oligo as primer produced three times higher yield of concatemers compared to sequence specific primer (Barumini_RCA_v2). The RCA product was also digested with HindIII to confirm that the concatemers release ~100 nt long monomers.

100 μl of streptavidin-coated Dynabeads M280 were washed three times and resuspended in 150 mM NaCl buffer (150 mM NaCl, 10 mM Tris pH 8.0, 1 mM EDTA). 2 μl RCA products containing 6.8 ng of ssDNA generated using the dA15 oligo or 2.6 ng of ssDNA produced by specific primer were bound on to streptavidin beads for 30 min at 25° C. Beads were washed one time each in 1M NaCl buffer (1M NaCl, 10 mM Tris pH 8.0, 1 mM EDTA), 150 mM NaCl buffer and 1× CutSmart buffer (NEB) to remove unbound products. ssDNAs were digested on beads with 20 U of HindIII-HF for 30 min at 37° C. Beads were washed one time each in 1M NaCl buffer, 150 mM NaCl buffer and 1× T4 DNA ligase buffer (NEB). 50 pmol each of phos-UMI_v2F and UMI_v2R UMI oligos were denatured at 95° C. for 3 min and annealed by cooling slowly to 12° C. at 1 C/sec. 2 pmol of annealed UMI oligos were ligated on to the HindIII digested beads using 4000 U T4 DNA ligase at 25° C. for 15 min at 1000 rpm. The ligation reaction was stopped by washing beads one time each in 1M NaCl buffer, 150 mM NaCl buffer and 1× T4 DNA ligase buffer (NEB). UMI ligated BarUMIni beads were phosphorylated using 50 U of T4 PNK and 2 mM ATP at 37 C for 30 min at 1000 rpm. The PNK reaction was stopped by washing the beads one time each in 1M NaCl buffer and 150 mM NaCl buffer. The final UMI ligated BarUMIni beads contain 5' GATC overhangs and are ready to use in downstream applications and can be stored at 4° C. until use.

TABLE 1

Oligonucleotide sequences

| Oligo name | Sequence (5' to 3') |
|---|---|
| Barumini_v2b (SEQ ID NO: 2) | TTTTTTTTT*ACACTCTTTCCCTACACGACGCTCTTCCGATCT*NNNVN NNVNNNVNNGCGCGCAAGCTTGCGCGCTCACTAAAGGACGCGCAAGCT TGCGCGCCAGGAAACAGCTATGACTTTTTTTTT |
| Splint_oligo (dA15) (SEQ ID NO: 3) | AAAAAAAAAAAAAAA |
| Barumini_RCA_v2 (SEQ ID NO: 4) | GTCATAGCTGTTTCCTG |
| UMI_v2F (SEQ ID NO: 5) | AGCTTGCCGVNNVNNNBNNBCGCGCG |
| UMI_v2R (SEQ ID NO: 6) | GATCCGCGCGVNNVNNNBNNBCGGCA |

TABLE 1-continued

Oligonucleotide sequences

| Oligo name | Sequence (5' to 3') |
|---|---|
| P7_PCRarm (SEQ ID NO: 7) | GTGACTGGAGTTCAGACGTGTGCTCTTCCGATCT |
| P7_splint (SEQ ID NO: 8) | GATCAGATCGGAAGAG |

*Barumini_v2b oligonucleotide: bold + italic = P5 adapter sequence; bold + italic + underline = barcode; underline = stem sequence; bold + underline = restriction enzyme site; italic = loop; and italic + underline = spacer region
*V = any of the three bases A, C or G
*B = any of the three bases C, G or T

Example 2—Barcoded Bead Validation

The present example involves the validation of the barcoded beads prepared according to Example 1.

The barcoded beads were validated by ligating naked genomic DNA (gDNA) as insert. 5 µg of GM12878 genomic DNA was digested with 50 U of DpnII enzyme at 37° C. overnight and dephosphorylated using 50 U of FastAP at 37° C. for 30 min. 500 ng of DpnII-digested, dephosphorylated gDNA was ligated on to BarUMIni beads using 4000 U of T4 DNA ligase at 25° C. for 15 min at 1000 rpm. gDNA ligated beads were washed one time each in 1M NaCl buffer, 150 mM NaCl buffer and 1× T4 DNA ligase buffer (NEB). gDNA ends were phosphorylated using 50 U T4 PNK and 2 mM ATP at 37° C. for 30 min at 1000 rpm. PNK reaction was stopped by washing beads one time each in 1M NaCl buffer and 150 mM NaCl buffer. 50 pmol each of P7_PCRarm and P7_splint oligos were denatured at 95° C. for 3 min and annealed by cooling slowly to 12° C. at 1 C/sec. 5 pmol of annealed P7 oligos were ligated on to distal ends of gDNA on beads using 4000 U of T4 DNA ligase at 25° C. for 15 min at 1000 rpm. The ligation reaction was stopped by washing the beads one time each in 1M NaCl buffer, 150 mM NaCl buffer and beads were resuspended in 150 mM NaCl buffer. Final library was PCR amplified using 2× KAPA HiFi PCR mix with P5 and P7 index primers for 18 cycles. PCR products were 0.8× SPRI bead cleaned up and quality assessed by running in a Fragment Analyzer. Libraries were sequenced on a Miseq sequencing system to generate about 300,000 reads for each library. The results are summarized in the table below.

| Experimental conditions | Raw reads | Reads with Barcode, UMI and gDNA insert | Reads with Barcode and UMI without insert | Total Barcoded reads |
|---|---|---|---|---|
| RCA using dA15 primer | 331,897 | 81.2% | 10.1% | 91.3% |
| RCA using specific primer | 463,020 | 78.8% | 11.6% | 90.4% |

Example 3—Haplotype Phasing

The present example is an example protocol which may be employed for haplotype phasing using the barcoded solid supports of the present disclosure.

1. Live cells are crosslinked with 1% formaldehyde at optimal time and temperature (15 min at room temperature) to preserve the contiguity and proximity of haplotypes and other higher order chromosomal interactions. Formaldehyde is quenched by 2.5M glycine buffer to prevent any further crosslinking with downstream enzymes.
2. Crosslinked cells are extracted with SDS to remove cellular proteins and preserve only crosslinked DNA/chromatin.
3. The crosslinked chromatin is digested with a RE whose recognition site occurs frequently in the genome (DpnII recognizing 5'-GATC site, for example). Sticky ends produced by the RE must be compatible with the 5'-overhangs on the BarUMIni beads.
4. 5' phosphate groups of digested DNA/chromatin are dephosphorylated using enzymes like Alkaline phosphatase. This is essential to facilitate strand specific ligation to the barcoded-adapters on beads. Dephosphorylation also prevents self-ligation and concatenation of genomic DNA.
5. Only the 3' ends of digested chromatin are then ligated to 5' ends of barcoded-adapters on the BarUMIni beads with compatible sticky ends. Excess chromatin/DNA is washed off using buffers with varying salt concentration.
6. Free 5' end of chromatin/DNA which is distal to the barcoded-adapter is then re-phosphorylated using T4 PNK.
7. Illumina P7 adapter (5'-GTGACTGGAGTTCAGACGTGTGCTCTTCCGATCT; SEQ ID NO: 7) is ligated to the distal 5' end of DNA/chromatin facilitated by a splint oligo (P7-splint: 5'-GATCAGATCGGAAGAG; SEQ ID NO: 8).
8. BarUMIni ligated DNA is extracted from chromatin protein complex by digestion with Proteinase K in the crosslink removal step.
9. Eluted library is then PCR amplified using Illumnia P5/P7 PCR primers. Indexed PCR primers can be used to multiplex sequence many samples together. PCR products float off of beads due to lack of binding ligand in the newly amplified DNA.
10. Final library is SPRI bead cleaned to remove excess PCR primers and adapter dimers. Library size range between 200-1000 bp with an average size of 500 bp. Library can be sequenced in standard Illumina sequencing machines.
11. Sequencing data are aligned to reference genome using BWA tool. Alignment SAM file is then analyzed using custom Python scripts to obtain barcode and UMI information.
12. Reads having same barcodes and thus 'linked-reads' are assigned to 'Barcode-islands' in the genome which indicate that these reads originated from same BarUMIni beads and are part of the initial long DNA molecule.

13. Overlapping barcode-islands are merged to form contigs or phase blocks. Continuous overlapping contigs are assembled to obtain haplotypes.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method of making a barcoded solid support, comprising:
producing a concatemer by rolling circle amplification (RCA) of a circular nucleic acid template, wherein the circular nucleic acid template comprises a barcode and a stem-loop forming region, and wherein the concatemer comprises a plurality of linked units, each unit comprising the barcode and a stem-loop structure formed from the stem-loop forming region; and
disposing the concatemer on a solid support, wherein:
the concatemer comprises a plurality of first binding members;
the solid support is functionalized with a plurality of second binding members having affinity for the first binding members; and
disposing the concatemer on the solid support comprises binding the first binding members to the second binding members.

2. The method according to claim 1, further comprising, prior to producing the concatemer, producing the circular nucleic acid template by circularizing a linear nucleic acid comprising the barcode and the stem-loop forming region.

3. The method according to claim 2, wherein the circularizing is by splint ligation.

4. The method according to claim 1, wherein disposing the concatemer on the solid support further comprises non-covalently binding the first binding members to the second binding members.

5. The method according to claim 4, wherein the first binding members comprise biotin and the second binding members comprise streptavidin, avidin, or anti-biotin antibodies.

6. The method according to claim 1, wherein the first binding members are enriched in regions between the stem-loop structures of the concatemer.

7. The method according to claim 1, wherein the first binding members are incorporated into the concatemer during RCA of the circular nucleic acid template.

8. The method according to claim 7, wherein nucleotides comprising the first binding members are incorporated into the concatemer during RCA of the circular nucleic acid template.

9. The method according to claim 8, wherein the nucleotides are biotinylated nucleotides.

10. The method according to claim 1, wherein the circular nucleic acid template further comprises a sequencing adapter such that each of the plurality of linked units of the concatemer further comprises the sequencing adapter.

11. The method according to claim 1, further comprising treating the stem-loop structures with an agent that produces stem structures having blunt ends or overhangs compatible with target nucleic acids.

12. The method according to claim 11, wherein the stem-loop structures comprise a recognition site for a restriction enzyme, and wherein the treating comprises contacting the stem-loop structures with the restriction enzyme to produce stem structures having ends compatible with the target nucleic acids.

13. The method according to claim 11, wherein the target nucleic acids comprise a unique molecular identifier (UMI), genomic DNA, mitochondrial DNA (mtDNA), cell-free DNA (cfDNA), complementary DNA (cDNA), RNA, or any combination thereof.

14. The method according to claim 11, further comprising ligating the target nucleic acids to the stem structures.

15. The method according to claim 11, further comprising ligating unique molecular identifiers (UMIs) to the stem structures.

16. The method according to claim 1, wherein the solid support comprises a bead.

* * * * *